tion effluent for analysis purposes. A radiant furnace was used to maintain a constant temperature during the reaction period. The temperature was measured with a thermocouple in a temperature well located on the lower outside wall of the reactor.

B. Toluene Conversion

The reaction was conducted in the stoichiometric mode of operation unless otherwise noted. The reactor was charged with approximately 11 milliliters of the inorganic metal/oxygen composition prepared as described in Examples 1 and 2 above. Glass wool plugs were used as supports for the composition. The charged reactor was placed in a radiant furnace and heated to maintain a constant temperature throughout the reaction period. Steam and toluene in a 2:1 mole ratio were fed to the reactor at a pressure of $1.013 \times 10^5$ pascal (1 atmosphere) at a rate sufficient to provide a reactor resident (contact) time of 4 seconds (unless otherwise noted) for the toluene (assuming a 50% void space in the reactor). After the reaction had proceeded for 1 minute, the reaction effluent, diluted with helium, was analyzed by gas-liquid chromatography. The results are tabulated in Table 2.

TABLE 2

| SAMPLE NO. | TEMPERATURE, °C./ CONTACT TIME seconds[1] | CONVERSION % | SELECIVITY, % STILBENE | BIBENZYL | BENZENE | STILBENE + BIBENZYL |
|---|---|---|---|---|---|---|
| 1-A-1-(a) | 630 | 92.0 | 24.5 | 2.7 | 21.8 | 27.2 |
|  | 570 | 49.5 | 34.4 | 23.2 | 10.7 | 57.6 |
|  | 450 | 13.2 | 14.1 | 26.6 | 3.4 | 40.7 |
| 1-A-1-(b) | 630 | 95.7 | 18.5 | 0.6 | 23.3 | 19.1 |
|  | 570 | 80.3 | 55.5 | 3.7 | 9.8 | 59.2 |
|  | 450 | 20.7 | 27.3 | 23.3 | 5.7 | 50.6 |
| 1-A-1-(c) | 630 | 50.0 | 18.1 | 13.7 |  |  |
| 1-A-2-(c) |  | 31.8 |  |  |  |  |
|  | 570 | 5.3 | 6.5 | 69.0 | 21.5 | 75.5 |
|  | 480 | 0.6 | 0.0 | 26.7 | 61.8 | 26.7 |
| 1-A-1-(d) | 630 | 8.7 | 7.6 | 19.9 | 28.0 | 27.5 |
|  | 570 | 10.1 | 7.7 | 17.5 | 41.5 | 25.2 |
|  | 450 | 3.1 | 2.5 | 6.7 | 45.0 | 9.2 |
| 1-A-1-(e) | 630 | 23.8 | 6.1 | 16.1 | 37.1 | 22.2 |
|  | 570 | 8.5 | 4.9 | 21.6 | 33.4 | 26.5 |
|  | 450 | 7.8 | 1.0 | 11.0 | 9.4 | 12.0 |
| 1-A-2-(a) | 600 | 62.0 | 11.3 | 15.5 | 21.6 | 26.8 |
|  | 480 | 13.4 | 21.9 | 48.4 | 4.4 | 70.3 |
|  | 450 | 5.7 | 13.1 | 62.0 | 3.6 | 75.1 |
| 1-A-2-(b) | 600 | 65.9 | 26.9 | 14.0 | 15.6 | 40.9 |
|  | 510 | 17.1 | 28.3 | 44.3 | 8.2 | 72.6 |
|  | 450 | 5.5 | 15.4 | 61.3 | 9.4 | 76.7 |
| 1-A-2-c) | 600 | 95.8 | 30.7 | 0.1 | 26.0 | 30.8 |
|  | 510 | 31.4 | 44.8 | 15.4 | 7.3 | 60.2 |
|  | 450 | 6.7 | 15.7 | 36.0 | 8.6 | 51.7 |
| 1-A-2-(d) | 600 | 44.1 | 38.8 | 2.0 | 30.5 | 40.8 |
|  | 510 | 27.5 | 72.2 | 4.7 | 11.6 | 76.9 |
|  | 450 | 24.2 | 33.0 | 16.2 | 4.3 | 49.2 |
| 1-A-2-(e) | 600 | 7.2 | 21.4 | 2.7 | 38.4 | 24.1 |
|  | 510 | 2.3 | 44.8 | 12.0 | 29.4 | 56.8 |
|  | 450 | 3.3 | 27.0 | 15.2 | 50.3 | 42.2 |
| 1-A-2-(f) | 600 | 7.6 | 24.5 | 0.0 | 37.3 | 24.5 |
|  | 510 | 2.3 | 44.4 | 3.3 | 37.5 | 47.7 |
|  | 450 | 1.3 |  |  |  |  |
| 1-A-3-(a) | 630 | 83.2 | 47.2 | 2.0 | 34.0 | 49.2 |
|  | 570 | 5.2 | 45.0 | 3.1 | 35.6 | 48.1 |
|  | 450 | 17.1 | 0.8 | 0.5 | 45.9 | 1.3 |
| 1-A-4-(a) | 630 | 51.4 | 23.3 | 0.7 | 52.4 | 24.0 |
|  | 570 | 29.0 | 46.1 | 0.2 | 39.4 | 46.3 |
|  | 450 | 23.9 | 21.5 | 8.3 | 27.4 | 29.8 |
| 1-B-1-(a) | 630 | 61.1 | 26.2 | 0.7 | 69.2 | 26.9 |
|  | 570 | 40.2 | 51.5 | 1.3 | 38.2 | 52.8 |
|  | 450 | 53.7 | 9.0 | 0.9 | 83.7 | 9.9 |
| 1-B-2-(a) | 630 | 41.1 | 39.5 | 0.1 | 35.7 | 39.6 |
|  | 570 | 28.2 | 41.8 | 1.9 | 28.8 | 43.7 |
|  | 450 | 14.4 | 69.0 | 0.8 | 25.7 | 69.8 |
| 1-B-3-(a) | 630 | 43.1 | 4.6 | 0.3 | 91.3 | 4.9 |
|  | 570 | 43.6 | 26.2 | 0.8 | 64.5 | 27.0 |
|  | 450 | 10.0 | 48.9 | 3.2 | 40.5 | 52.1 |

[1] A contact time of 4 seconds was employed unless otherwise noted.

Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for dehydrocoupling toluene which comprises contacting the toluene in the vapor phase at a temperature between about 450° C. and about 650° C. with an inorganic metal/oxygen composition represented by the empirical formula:

HYDROCARBON DEHYDROGENATION WITH A NONACIDIC MULTIMETALLIC CATALYTIC COMPOSITE

CROSS-REFERENCE TO RELATED APPLICATIONS

This application is a division of my prior, copending application Ser. No. 936,428 filed Aug. 24, 1978; which in turn is a continuation-in-part of my prior application Ser. No. 786,744 filed Apr. 11, 1977 and issued Aug. 29, 1978 as U.S. Pat. No. 4,110,201; and which in turn is a division of my prior application Ser. No. 621,718 filed Oct. 14, 1975 and now abandoned. All of the teachings of these prior applications are specifically incorporated herein by reference.

The subject of the present invention is, broadly, an improved method for dehydrogenating a dehydrogenatable hydrocarbon to produce a hydrocarbon product containing the same number of carbon atoms but fewer hydrogen atoms. In another aspect, the present invention involves a method of dehydrogenating normal paraffin hydrocarbons containing 4 to 30 carbon atoms per molecule to the corresponding normal mono-olefin with minimum production of side products. In yet another aspect, the present invention relates to a novel nonacidic multimetallic catalytic composite comprising a combination of catalytically effective amounts of a platinum group component, a cobalt component, a cadmium component, and an alkali or alkaline earth component with a porous carrier material. This nonacidic composite has highly beneficial characteristics of activity, selectivity, and stability when it is employed in the dehydrogenation of dehydrogenatable hydrocarbons such as aliphatic hydrocarbons, naphthene hydrocarbons, and alkylaromatic hydrocarbons.

The conception of the present invention followed from my search for a novel catalytic composite possessing a hydrogenation-dehydrogenation function, a controllable cracking function, and superior conversion, selectivity, and stability characteristics when employed in hydrocarbon conversion processes that have traditionally utilized dual-function catalytic composites. In my prior applications, I disclosed a significant finding with respect to a multimetallic catalytic composite meeting these requirements. More specifically, I determined that a combination of cobalt and cadmium can be utilized, under certain specified conditions, to beneficially interact with the platinum group component of a dual-function catalyst with a resulting marked improvement in the performance of such a catalyst. Now I have ascertained that a catalytic composite, comprising a combination of catalytically effective amounts of a platinum group component, a cobalt component, and a cadmium component with a porous carrier material can have superior activity, selectivity and stability characteristics when it is employed in a hydrocarbon dehydrogenation process if these components are uniformly dispersed in the porous carrier material in the amounts specified hereinafter and if the oxidation state of the metallic ingredients are carefully controlled so that substantially all of the platinum group component is present in the elemental metallic state, substantially all of the cadmium component is preferably present in a positive oxidation state, and substantially all of the catalytically available cobalt component is present in the elemental metallic state or in a state which is reducible to the elemental metallic state under dehydrogenation conditions or in a mixture of these states. I have discerned, moreover, that a particularly preferred multimetallic catalytic composite of this type contains not only a platinum group component, a cobalt component, and a cadmium component, but also an alkali or alkaline earth component in an amount sufficient to ensure that the resulting catalyst is nonacidic.

The dehydrogenation of dehydrogenatable hydrocarbons is an important commercial process because of the great and expanding demand for dehydrogenated hydrocarbons for use in the manufacture of various chemical products such as detergents, plastics, synthetic rubbers, pharmaceutical products, high octane gasolines, perfumes, drying oils, ion-exchange resins, and various other products well known to those skilled in the art. One example of this demand is in the manufacture of high octane gasoline by using $C_3$ and $C_4$ mono-olefins to alkylate isobutane. Another example of this demand is in the area of dehydrogenation of normal paraffin hydrocarbons to produce normal mono-olefins having 4 to 30 carbon atoms per molecule. These normal mono-olefins can, in turn, be utilized in the synthesis of a vast number of other chemical products. For example, derivatives of normal mono-olefins have become of substantial importance to the detergent industry where they are utilized to alkylate an aromatic, such as benzene, with subsequent transformation of the product arylalkane into a wide variety of biodegradable detergents such as the alkylaryl sulfonate types of detergents which are most widely used today for household, industrial, and commercial purposes. Still another large class of detergents produced from these normal mono-olefins are the oxyalkylated phenol derivatives in which the alkylphenol base is prepared by the alkylation of phenol with these normal mono-olefins. Still another type of detergents produced from these normal mono-olefins are the biodegradable alkylsulfonates formed by the direct sulfation of the normal mono-olefins. Likewise, the olefin can be subjected to direct sulfonation with sodium bisulfite to make biodegradable alkylsulfonates. As a further example, these mono-olefins can be hydrated to produce alcohols which then, in turn, can be used to produce plasticizers and/or synthetic lube oils.

Regarding the use of products made by the dehydrogenation of alkylaromatic hydrocarbons, they find wide application in the petroleum, petrochemical, pharmaceutical, detergent, plastic, and the like industries. For example, ethylbenzene is dehydrogenated to produce styrene which is utilized in the manufacture of polystyrene plastics, styrene-butadiene rubber, and the like products. Isopropylbenzene is dehydrogenated to form alpha-methylstyrene which, in turn, is extensively used in polymer formation and in the manufacture of drying oils, ion-exchange resins, and the like materials.

Responsive to this demand for these dehydrogenation products, the art has developed a number of alternative methods to produce them in commercial quantities. One method that is widely utilized involves the selective dehydrogenation of a dehydrogenatable hydrocarbon by contacting the hydrocarbon with a suitable catalyst at dehydrogenation conditions. As is the case with most catalytic procedures, the principal measure of effectiveness for this dehydrogenation method involves the ability to perform its intended function with minimum interference of side reactions for extended periods of time. The analytical terms used in the art to broadly measure how well a particular catalyst performs its intended ingredients, suitable methods of multimetallic composite preparation, suitable dehydrogenatable hydrocarbons, operating conditions for use in the dehydrogenation process, and the like particulars. These are hereinafter given in the following detailed discussion of each of these facets of the present invention. It is to be understood that (1) the term "nonacidic" means that the catalyst produces less than 10% conversion of 1-butene to isobutylene when tested at dehydrogenation conditions and, preferably, less than 1% and (2) the expression "uniformly dispersed throughout a carrier material" is intended to mean that the amount of the subject component, expressed on a weight percent basis, is approximately the same in any reasonably divisible portion of the carrier material as it is in gross.

Regarding the dehydrogenatable hydrocarbon that is subjected to the method of the present invention, it can, in general, be an organic compound having 2 to 30 carbon atoms per molecule and containing at least one pair of adjacent carbon atoms having hydrogen attached thereto. That is, it is intended to include within the scope of the present invention, the dehydrogenation of any organic compound capable of being dehydrogenated to produce products containing the same number of carbon atoms but fewer hydrogen atoms; and capable of being vaporized at the dehydrogenation temperatures used herein. More particularly, suitable dehydrogenatable hydrocarbons are: aliphatic compounds containing 2 to 30 carbon atoms per molecule, alkylaromatic hydrocarbons where the alkyl group contains 2 to 6 carbon atoms, and naphthenes or alkyl-substituted naphthenes. Specific examples of suitable dehydrogenatable hydrocarbons are: (1) alkanes such as ethanes, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, and the like compounds; (2) naphthenes such as cyclopentane, cyclohexane, methylcyclopentane, ethylcyclopentane, n-propylcyclopentane, 1,3-dimethylcyclohexane, and the like compounds; and (3) alkylaromatics such as ethylbenzene, n-butylbenzene, 1,3,5-triethylbenzene, isopropylbenzene, isobutylbenzene, ethylnaphthaline, and the like compounds.

In a preferred embodiment, the dehydrogenatable hydrocarbon is a normal paraffin hydrocarbon having about 4 to 30 carbon atoms per molecule. For example, normal paraffin hydrocarbons containing about 10 to 18 carbon atoms per molecule are dehydrogenated by the subject method to produce the corresponding normal mono-olefin which can, in turn, be alkylated with benzene and sulfonated to make alkylbenzene sulfonate detergents having superior biodegradability. Likewise, n-alkanes having 10 to 18 carbon atoms per molecule can be dehydrogenated to the corresponding normal mono-olefin which, in turn, can be sulfonated or sulfated to make excellent detergents. Similarly, n-alkanes having 6 to 10 carbon atoms can be dehydrogenated to form the corresponding mono-olefin which can, in turn, be hydrated to produce valuable alcohols. Preferred feed streams for the manufacture of detergent intermediates contain a mixture of 4 or 5 adjacent normal paraffin homologues such as $C_{10}$ to $C_{13}$, $C_{11}$ to $C_{14}$, $C_{11}$ to $C_{15}$ and the like mixtures.

The multimetallic catalyst used in the present invention comprises a porous carrier material or support having combined therewith a uniform dispersion of catalytically effective amounts of a platinum group component, a cobalt component, a cadmium component and, in the preferred case, an alkali or alkaline earth component.

Considering first the porous carrier material utilized in the present invention, it is preferred that the material be a porous adsorptive, high-surface area support having a surface area of about 25 to about 500 $m^2/g$. The porous carrier material should be relatively refractory to the conditions utilized in the dehydrogenation process, and it is intended to include within the scope of the present invention carrier materials which have traditionally been utilized in dual-function hydrocarbon conversion catalysts, such as: (1) activated carbon, coke, charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, aluminaboria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $MnAl_2O_4$, $CaAl_2O_4$ and other like compounds having the formula $MO.Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as the gamma-, eta-, and theta-alumina, with gamma- or eta-alumina giving best results. In addition, in some embodiments the alumina carrier material may contain minor proportions of other well-known refractory inorganic oxides such as silica, zirconia, magnesia, etc.; however, the preferred support is substantially pure gamma- or eta-alumina. Preferred carrier materials have an apparent bulk density of about 0.2 to about 0.7 g/cc and surface area characteristics such that the average pore diameter is about 20 to about 300 Angstroms, the pore volume (B.E.T.) is about 0.1 to about 1 cc/g and the surface area (B.E.T) is about 100 to about 500 $m^2/g$. In general, best results are typically obtained with a gamma-alumina carrier material which is used in the form of spherical particles having: a relatively small diameter (i.e. typically about 1/16 inch), an apparent bulk density of about 0.2 to about 0.6 (most preferably about 0.3) g/cc, a pore volume (B.E.T.) of about 0.4 cc/g, and a surface area (B.E.T.) of about 100 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, etc., and utilized in any desired size. For the purpose of the present invention, a particularly preferred form of alumina is the sphere; and alumina spheres may be continuously manufactured by the well-known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. It is a good practice to subject the calcined particles to a high temperature treatment with steam in order to remove undesired acidic components such as residual chloride. This procedure effects conversion of the alumina hydrogel to the corresponding crystalline gamma-alumina. See the teachings of U.S. Pat. No. 2,620,314 for additional details.

The expression "catalytically available cobalt" as used herein is intended to mean the portion of the cobalt component that is available for use in accelerating the dehydrogenation reaction of interest. For certain types of carrier materials which can be used in the preparation of the instant catalyst composite, it has been observed that a portion of the cobalt incorporated therein is essentially bound-up in the crystal structure thereof in a manner which essentially makes it catalytically unavailable; in fact it is more a part of the refractory carrier material than a catalytically active component. Specific examples of this effect are observed when the carrier material can form a spinel or spinel-like structure with a portion of the cobalt component and/or when a refractory cobalt oxide or aluminate is formed by reaction of the carrier material (or precursor thereof) with a portion of the cobalt component. When this effect occurs, it is only with great difficulty that the portion of the cobalt bound-up with the support can be reduced to a catalytically active state and the conditions required to do this are beyond the severity levels normally associated with dehydrogenation conditions and are in fact likely to seriously damage the necessary porous characteristics of the support. In the cases where cobalt can interact with the crystal structure of the support to render a portion thereof catalytically unavailable, the concept of the present invention merely requires that the amount of cobalt added to the subject catalyst be adjusted to satisfy the requirements of the support as well as the catalytically available cobalt requirements of the present invention. Against this background then, the hereinafter stated specifications for oxidation state, particle size and dispersion of the cobalt component are to be interpreted as directed to a description of the catalytically available cobalt. On the other hand, the specifications for the amount of cobalt used are to be interpreted to include all of the cobalt contained in the catalyst in any form.

One essential constituent of the acidic multimetallic catalyst of the present invention is a cadmium component. This component may in general be present in the instant catalytic composite in any catalytically available form such as the elemental metal, a compound like the oxide, hydroxide, halide, oxyhalide, aluminate, or in chemical combination with one or more of the other ingredients of the catalyst. Although it is not intended to restrict the present invention by this explanation, it is believed that best results are obtained when the cadmium component is present in the composite in a form wherein substantially all of the cadmium moiety is in an oxidation state above that of the elemental metal such as in the form of cadmium oxide or cadmium aluminate or in a mixture thereof and the subsequently described oxidation and reduction steps that are preferably used in the preparation of the instant catalytic composite are specifically designed to achieve this end. The term "cadmium aluminate" as used herein refers to a coordinated complex of cadmium, oxygen, and aluminum which are not necessarily present in the same relationship for all cases covered herein. This cadmium component can be used in any amount which is catalytically effective, with good results obtained, on an elemental basis, with about 0.01 to about 5 wt. % cadmium in the catalyst. Best results are ordinarily achieved with about 0.05 to about 1 wt. % cadmium, calculated on an elemental basis.

This cadmium component may be incorporated in the catalytic composite in any suitable manner known to the art to result in a relatively uniform dispersion of the cadmium moiety in the carrier material, such as by coprecipitation or cogellation or coextrusion with the porous carrier material, ion exchange with the gelled carrier material, or impregnation with the carrier material either after, before, or during the period when it is dried and calcined. It is to be noted that it is intended to include within the scope of the present invention all conventional methods for incorporating and simultaneously uniformly distributing a metallic component in a catalytic composite and the particular method of incorporation used is not deemed to be an essential feature of the present invention. One method of incorporating the cadmium component into the catalytic composite involves cogelling or coprecipitating the cadmium component in the form of the corresponding hydrous oxide during the preparation of the preferred carrier material, alumina. This method typically involves the addition of a suitable sol-soluble or sol-dispersible cadmium compound such as cadmium acetate, cadmium nitrate, and the like to the alumina hydrosol and then combining the hydrosol with a suitable gelling agent and dropping the resulting mixture into an oil bath, etc., as explained in detail hereinafter. Alternatively, the cadmium compound can be added to the gelling agent. After drying and calcining the resulting gelled carrier material in air, there is obtained an intimate combination of alumina and cadmium oxide and/or aluminate. A preferred method of incorporating the cadmium component into the catalytic composite involves utilization of a soluble, decomposable compound of cadmium to impregnate the porous carrier material. In general, the solvent used in this impregnation step is selected on the basis of the capability to dissolve the desired cadmium compound without adversely affecting the carrier material or the other ingredients of the catalyst—for example, a suitable alcohol, ether, acid and the like solvents. The solvent is preferably an aqueous, acidic solution. Thus, the cadmium component may be added to the carrier material by commingling the latter with an aqueous acidic solution of suitable cadmium salt, complex, or compound such as cadmium acetate, cadmium ammonium chloride, cadmium benzoate, cadmium bromide, cadmium chlorate, cadmium chloroplatinate, cadmium fluoride, cadmium formate, cadmium iodide, cadmium lactate, cadmium nitrate, cadmium bromate, cadmium hydroxide, any of the soluble tetrammine cadmium salts, and the like compounds. A particularly preferred impregnation solution comprises an acidic aqueous solution of cadmium acetate or nitrate. Suitable acids for use in the impregnation solution are: inorganic acids such as hydrochloric acid, nitric acid, and the like, and strongly acidic organic acids such as oxalic acid, malonic acid, citric acid, and the like. In general, the cadmium component may be impregnated either prior to, simultaneously with, or after the other ingredients are added to the carrier material. However, excellent results are obtained when the cadmium component is impregnated simultaneously with the platinum group component. In fact the preferred preparation procedure for the instant catalytic composite involves a two-step impregnation technique wherein the first impregnation step uses an aqueous impregnation solution containing the desired amounts of chloroplatinic acid, cadmium nitrate or acetate and nitric acid.

A second essential ingredient of the subject catalyst is the platinum group component. That is, it is intended to cover the use of platinum, iridium, osmium, ruthenium, rhodium, palladium, or mixtures thereof as a second component of the present composite. It is an essential feature of the present invention that substantially all of this platinum group component exists within the final catalytic composite in the elemental metallic state. Generally, the amount of this component present in the final catalytic compsosite is small compared to the quantities of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of platinum, iridium, rhodium, or palladium metal. Particularly preferred mixtures of these metals are platinum and iridium and platinum and rhodium.

This platinum group component may be incorporated in the catalytic composite in any suitable manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chloropalladic acid. Other water-soluble compounds or complexes of platinum group metals may be employed in impregnation solutions and include ammonium chloroplatinate, bromoplatinic acid, platinum trichloride, platinum tetrachloride hydrate, platinum dichlorocarbonyl dichloride, dinitrodiaminoplatinum, sodium tetranitroplatinate (II), palladium chloride, palladium nitrate, palladium dioxide, diamminepalladium (II) hydroxide, tetramminepalladium (II) chloride, hexamminerhodium chloride, rhodium carbonylchloride, rhodium trichloride hydrate, rhodium nitrate, sodium hexachlorohodate (III), sodium hexanitrorhodate (III), iridium tribromide, iridium dichloride, iridium tetrachloride, sodium hexanitroiridate (III), potassium chloroiridate, potassium rhodium oxalate, etc. The utilization of a platinum, iridium, rhodium, or palladium chloride compound, such as chloroplatinic, chloroiridic, or chloropalladic acid or rhodium trichloride hydrate, is ordinarily preferred. Hydrogen chloride, nitric acid, or the like acid is also generally added to the impregnation solution in order to further facilitate the uniform distribution of the metallic components throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

A third essential ingredient of the instant multimetallic catalytic composite is a cobalt component. Although this component may be initially incorporated into the composite in many different decomposable forms which are hereinafter stated, my basic finding is that the catalytically active state for hydrocarbon conversion with this component is the elemental metallic state. Consequently, it is a feature of this invention that substantially all of the catalytically available cobalt component exists in the catalytic composite either in the elemental metallic state or in a state which is reducible to the elemental state under hydrocarbon dehydrogenation conditions or in a mixture of these states. Examples of this last state are obtained when the catalytically available cobalt component is initially present in the form of cobalt oxide, hydroxide, halide, oxyhalide, and the like reducible compounds. As a corollary to this basic finding on the active state of the catalytically available cobalt component, it follows that the presence of the catalytically available cobalt in forms which are not reducible at hydrocarbon dehydrogenation conditions is to be scrupulously avoided if the full benefits of the present invention are to be realized. Illustrative of these undesired forms are cobalt sulfide and the cobalt oxysulfur compounds such as cobalt sulfate. Best results are obtained when the composite initially contains all of the catalytically available cobalt component in the elemental metallic state or in a reducible oxide state or in a mixture of these states. All available evidence indicates that the preferred preparation procedure specifically described in Example I results in a catalyst having the catalytically available cobalt component present in the form of a mixture of the reducible oxide and the elemental metal. Based on the performance of such a catalyst, it is believed that substantially all of this reducible oxide form of the cobalt component is reduced to the elemental metallic state when a dehydrogenation process using this catalyst is started-up and lined-out at hydrocarbon dehydrogenation conditions. The cobalt component may be utilized in the composite in any amount which is catalytically effective, with the preferred amount being about 0.05 to about 5 wt. % thereof, calculated on an elemental cobalt basis. Typically, best results are obtained with about 0.1 to about 2.5 wt. % cobalt. It is, additionally, preferred to select the specific amount of cobalt from within this broad weight range as a function of the amount of the platinum group component, on an atomic basis, as is explained hereinafter.

The cobalt component may be incorporated into the catalytic composite in any suitable manner known to those skilled in the catalyst formulation art to result in a relatively uniform distribution of the catalytically available cobalt in the carrier material such as coprecipitation, cogelation, ion-exchange, coextrusion, impregnation, etc. In addition, it may be added at any stage of the preparation of the composite—either during preparation of the carrier material or thereafter—since the precise method of incorporated used is not deemed to be critical. However, best results are obtained when the catalytically available cobalt component is relatively uniformly distributed throughout the carrier material in a relatively small particle or crystallite size having a maximum dimension of less than 100 Angstroms, and the preferred procedures are the ones that are known to result in a composite having a relatively uniform distribution of the catalytically available cobalt moiety in a relatively small particle size. One acceptable procedure for incorporating this component into the composite involves cogelling or coprecipitating the cobalt component during the preparation of the preferred carrier material, alumina. This procedure usually comprehends the addition of a soluble, decomposable, and reducible compound of cobalt such as cobalt acetate or chloride or nitrate to the alumina hydrosol before it is gelled. Alternatively, the reducible compound of cobalt can be added to the gelling agent before it is added to the hydrosol. The resulting mixture is then finished by conventional gelling, aging, drying, and calcination steps as explained hereinbefore. One preferred way of incorporating this component is an impregnation step wherein the porous carrier material is impregnated with a suitable cobalt-containing solution either before, during, or after the carrier material is calcined or oxidized. The solvent used to form the impregnation solution may be water, alcohol, ether, or any other suitable organic or inorganic solvent provided the solvent does not adversely interact with any of the other ingredients of the composite or interfere with the distribution and reduction of the cobalt component. Preferred impregnation solutions are aqueous solutions of water-soluble, decomposable, and reducible cobalt compounds such as cobaltous acetate, cobaltous benzoate, cobaltous bromate, cobaltous bromide, cobaltous chlorate and perchlorate, cobaltous chloride, cobaltic chloride, cobaltous fluoride, cobaltous iodide, cobaltous nitrate, hexamminecobalt (III) chloride, hexamminecobalt (III) nitrate, triethylenediamminecobalt (III) chloride, cobaltous hexamethylenetetramine, and the like compounds. Best results are ordinarily obtained when the impregnation solution is an aqueous solution of cobalt acetate or cobalt nitrate. This cobalt component can be added to the carrier material, either prior to, simultaneously with, or after the other metallic components are combined therewith. Best results are usually achieved when this component is added after the platinum group and cadmium components have been impregnated via an aqueous impregnation solution. In fact, excellent results are obtained, as reported in the examples, with a two step impregnation procedure using a second aqueous acidic impregnation solution containing cobalt acetate or nitrate and nitric acid.

A highly preferred ingredient of the catalyst used in the present invention is the alkali or alkaline earth component. More specifically, this component is selected from the group consisting of the compounds of the alkali metals—cesium, rubidium, potassium, sodium, and lithium—and of the alkaline earth metals—calcium, strontium, barium, and magnesium. This component exists within the catalytic composite in an oxidation state above that of the elemental metal such as a relatively stable compound such as the oxide or hydroxide, or in combination with one or more of the other components of the composite, or in combination with the carrier material such as, for example, in the form of an alkali or alkaline earth metal aluminate. Since, as is explained hereinafter, the composite containing the alkali or alkaline earth component is always calcined or oxidized in an air atmosphere before use in the dehydrogenation of hydrocarbons, the most likely state this component exists in during use in the dehydrogenation reaction is the corresponding metallic oxide such as lithium oxide, potassium oxide, sodium oxide, and the like. Regardless of what precise form in which it exists in the composite, the amount of this component utilized is preferably selected to provide a nonacidic composite containing about 0.1 to about 5 wt. % of the alkali metal or alkaline earth metal, and, more preferably, about 0.25 to about 3.5 wt. %. Best results are obtained when this component is a compound of lithium or potassium. The function of this component is to neutralize any of the acidic material such as halogen which may have been used in the preparation of the present catalyst so that the final catalyst is nonacidic.

This alkali or alkaline earth component may be combined with the porous carrier material in any manner known to those skilled in the art to result in a relatively uniform dispersion of this component throughout the carrier material with consequential neutralization of any acidic sites which may be present therein. Typically good results are obtained when it is combined by impregnation, coprecipitation, ion-exchange, and the like procedures. The preferred procedure, however, involves impregnation of the carrier material either before, during, or after it is calcined, or before, during, or after the other metallic ingredients are added to the carrier material. Best results are ordinarily obtained when this component is added to the carrier material after the platinum group and cadmium components because the alkali metal or alkaline earth metal component acts to neutralize the acidic materials used in the preferred impregnation procedure for these metallic components. In fact, it is preferred to add the platinum group and cadmium components to the carrier material, oxidize the resulting composite in a wet air stream at a high temperature (i.e. typically about 600° to 1000° F.), then treat the resulting oxidized composite with steam or a mixture of air and steam at a relatively high temperature of about 800° to about 1050° F. in order to remove at least a portion of any residual acidity and thereafter add the cobalt and the alkali metal or alkaline earth components. Typically, the impregnation of the carrier material with this component is performed by contacting the carrier material with a solution of a suitable decomposable compound or salt of the desired alkali or alkaline earth metal. Hence, suitable compounds include the alkali metal or alkaline earth metal halides, nitrates, acetates, carbonates, phosphates, and the like compounds. For example, excellent results are obtained by impregnating the carrier material after the platinum group and cadmium components have been combined therewith, with an aqueous solution of lithium nitrate or potassium nitrate and cadmium acetate or nitrate.

Regarding the preferred amounts of the metallic components of the subject catalyst, I have found it to be a beneficial practice to specify the amounts of these metallic components not only on an absolute basis but also as a function of the amount of the platinum group component, expressed on an atomic basis. Quantitatively, the amount of the cobalt component is preferably sufficient to provide an atomic ratio of cobalt to platinum group metal of about 0.1:1 to about 66:1, with best results obtained at an atomic ratio of about 0.4:1 to about 18:1. Similarly, it is a good practice to specify the amount of the cadmium component so that the atomic ratio of cadmium to platinum group metal contained in the composite is about 0.1:1 to about 5:1 with the preferred range being about 0.2:1 to about 2:1. In the same manner, the amount of the alkali or alkaline earth component is ordinarily selected to produce a composite having an atomic ratio of alkali metal or alkaline earth metal to platinum group metal of about 5:1 to about 100:1 or more, with the preferred range being about 10:1 to about 75:1.

Another significant parameter for the instant nonacidic catalyst is the "total metals content" which is defined to be the sum of the platinum group component, the cobalt component, the cadmium component, and the alkali or alkaline earth component, calculated on an elemental metal basis. Good results are ordinarily obtained with the subject catalyst when this parameter is fixed at a value of about 0.2 to about 5 wt. %, with best results ordinarily achieved at a metals loading of about 0.4 to about 4 wt. %.

Integrating the above discussion of each of the essential and preferred components of the catalytic composite used in the present invention, it is evident that an especially preferred nonacidic catalytic composite comprises a combination of a platinum group component, a cobalt component, a cadmium component, and an alkali or alkaline earth component with an alumina carrier material in amounts sufficient to result in the composite containing from about 0.05 to about 1 wt. % platinum group metal, about 0.1 to about 2.5 wt. % cobalt, about 0.25 to about 3.5 wt. % alkali metal or alkaline earth metal, and about 0.05 to about 1 wt. % cadmium.

Regardless of the details of how the components of the catalyst are combined with the porous carrier material, the resulting multimetallic composite generally will be dried at a temperature of about 200° F. to about 600° F. for a period of from about 2 to about 24 hours or more, and finally calcined or oxidized at a temperature of about 600° F. to about 1100° F. (preferably about 800° to about 950° F.) in an air atmosphere for a period of about 0.5 to 10 hours, preferably about 1 to about 5 hours, in order to convert substantially all the metallic components to the corresponding oxide form. When acidic components are present in any of the reagents used to effect incorporation of any one of the components of the subject composite, it is a good practice to subject the resulting composite to a high temperature treatment with steam or with a mixture of steam and air, either before, during or after this oxidation step in order to remove as much as possible of the undesired acidic component. For example, when the platinum group component is incorporated by impregnating the carrier material with chloroplatinic acid, it is preferred to subject the resulting composite to a high temperature treatment with steam or a mixture of steam and air at a temperature of about 600° to 1100° F. in order to remove as much as possible of the undesired chloride.

The resultant oxidized catalytic composite is preferably subjected to a substantially water-free reduction step prior to its use in the dehydrogenation of hydrocarbons. This step is designed to selectively reduce the platinum group component to the corresponding metal, while maintaining the cadmium component in a positive oxidation state, and to insure a uniform and finely divided dispersion of the metallic components throughout the carrier material. It is a good practice to dry the oxidized catalyst prior to this reduction step by passing a stream of dry air or nitrogen through same at a temperature of about 500° to 1100° F. (preferably about 800° to about 950° F.) and at a GHSV of about 100 to 800 hr.$^{-1}$ until the effluent stream contains less than 1000 ppm. of $H_2O$ and preferably less than 500 ppm. Preferably, a substantially pure and dry hydrogen stream (i.e. less than 20 vol. ppm. $H_2O$) is used as the reducing agent in this reduction step. The reducing agent is contacted with the oxidized catalyst at conditions including a temperature of about 600° F. to about 1200° F. (preferably about 800° to about 1000° F.), a GHSV of about 300 to 1000 hr.$^{-1}$, and a period of time of about 0.5 to 10 hours effective to reduce substantially all of the platinum group component to the elemental metallic state, while maintaining the cadmium component in an oxidation state above that of the elemental metal. This reduction treatment may be performed in situ as part of a start-up sequence if precautions are taken to predry the plant to a substantially water-free state and if a substantially water-free hydrogen stream is used.

Although using the subject catalyst in a substantially sulfur-free state is an especially preferred mode of operation for the present hydrocarbon dehydrogenation method (as explained in the teachings of my prior applications Ser. Nos. 786,744 and 621,718, the resulting selectively reduced catalytic composite may in some circumstances be beneficially subjected to a presulfiding operation designed to incorporate in the catalytic composite from about 0.01 to about 0.5 wt. % sulfur, calculated on an elemental basis. Preferably, this presulfiding treatment takes place in the presence of hydrogen and a suitable sulfur-containing sulfiding reagent such as hydrogen sulfide, lower molecular weight mercaptans, organic sulfides, etc. Typically, this procedure comprises treating the selectively reduced catalyst with a sulfiding reagent such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more. It is generally a good practice to perform this presulfiding step under substantially water-free conditions. Although not preferred, it is within the scope of the present invention to maintain or achieve the sulfided state of the instant catalyst during use in the dehydrogenation of hydrocarbons by continuously or periodically adding a decomposable sulfur-containing compound, such as the sulfiding reagents previously mentioned, to the reactor containing the catalyst in an amount sufficient to provide about 1 to 500 wt. ppm., preferably 1 to 20 wt. ppm. of sulfur based on hydrocarbon charge.

According to the method of the present invention, the dehydrogenatable hydrocarbon is contacted with the multimetallic catalytic composite described above in a dehydrogenation zone maintained at dehydrogenation conditions. This contacting may be accomplished by using the catalyst in a fixed bed system, a moving bed system, a fluidized bed system, or in a batch type operation; however, in view of the danger of attrition losses of the valuable catalyst and of well-known operational advantages, it is preferred to use a fixed bed system. In this system, the hydrocarbon feed stream is preheated by any suitable heating means to the desired reaction temperature and then passed into a dehydrogenation zone containing a fixed bed of the catalyst previously characterized. It is, of course, understood that the dehydrogenation zone may be one or more separate reactors with suitable heating means therebetween to insure that the desired conversion temperature is maintained at the entrance to each reactor. It is also to be noted that the reactants may be contacted with the catalyst bed in either upward, downward, or radial flow fashion with the latter being preferred. In addition, it is to be noted that the reactants may be in the liquid phase, a mixed liquid-vapor phase, or a vapor phase when they contact the catalyst, with best results obtained in the vapor phase.

Although hydrogen is the preferred diluent for use in the subject dehydrogenation method, in some cases other art-recognized diluents may be advantageously utilized, either individually or in admixture with hydrogen or each other, such as steam, methane, ethane, carbon dioxide, and the like diluents. Hydrogen is preferred because it serves the dual-function of not only lowering the partial pressure of the dehydrogenatable hydrocarbon, but also of suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of about 1.5:1 to about 10:1. The hydrogen stream charged to the dehydrogenation zone will typically be recycled hydrogen obtained from the effluent stream from this zone after a suitable hydrogen separation step. As is explained in my prior applications Ser. Nos. 786,744 and 621,718, a highly preferred mode of operation of the instant dehydrogenation method is in a substantially water-free environment; however, when utilizing hydrogen in the instant method, improved selectivity results are obtained under certain limited circumstances, if water or a water-producing substance (such as an alcohol, ketone, ether, aldehyde, or the like oxygen-containing decomposable organic compound) is added to the dehydrogenation zone in an amount calculated on the basis of equivalent water, corresponding to about 1 to about 5,000 wt. ppm. of the hydrocarbon charge stock, with about 1 to 1,000 wt. ppm. of water giving best results. This water addition feature may be used on a continuous or intermittent basis to regulate the activity and selectivity of the instant catalyst.

Regarding the conditions utilized in the method of the present invention, these are generally selected from the dehydrogenation conditions well known to those skilled in the art for the particular dehydrogenatable hydrocarbon which is charged to the process. More specifically, suitable conversion temperatures are selected from the range of about 700° to about 1200° F. with a value being selected from the lower portion of this range for the more easily dehydrogenated hydrocarbons such as the long chain normal paraffins and from the higher portion of this range for the more difficultly dehydrogenated hydrocarbons such as propane, butane, and the like hydrocarbons. For example, for the dehydrogenation of $C_6$ to $C_{30}$ normal paraffins, best results are ordinarily obtained at a temperature of about 800° to about 950° F. The pressure utilized is ordinarily selected at a value which is as low as possible consistent with the maintenance of catalyst stability and is usually about 0.1 to about 10 atmospheres with best results ordinarily obtained in the range of about 0.5 to about 3 atmospheres. In addition, a liquid hourly space velocity (calculated on the basis of the volume amount, as a liquid, of hydrocarbon charged to the dehydrogenation zone per hour divided by the volume of the catalyst bed utilized) is selected from the range of about 1 to about 40 hr.$^{-1}$, with best results for the dehydrogenation of long chain normal paraffins typically obtained at a relatively high space velocity of about 25 to 35 hr.$^{-1}$.

Regardless of the details concerning the operation of the dehydrogenation step, an effluent stream will be withdrawn therefrom. This effluent will usually contain unconverted dehydrogenatable hydrocarbons, hydrogen, and products of the dehydrogenation reaction. This stream is typically cooled and passed to a hydrogen-separating zone wherein a hydrogen-rich vapor phase is allowed to separate from a hydrocarbon-rich liquid phase. In general, it is usually desired to recover the unreacted dehydrogenatable hydrocarbon from this hydrocarbon-rich liquid phase in order to make the dehydrogenation process economically attractive. This recovery operation can be accomplished in any suitable manner known to the art such as by passing the hydrocarbon-rich liquid phase through a bed of suitable adsorbent material which has the capability to selectively retain the dehydrogenated hydrocarbons contained therein or by contacting same with a solvent having a high selectivity for the dehydrogenated hydrocarbon, or by a suitable fractionation scheme where feasible. In the case where the dehydrogenated hydrocarbon is a mono-olefin, suitable adsorbents having this capability are activated silica gel, activated carbon, activated alumina, various types of specially prepared zeolitic crystalline alumino-silicates, molecular sieves, and the like adsorbents. In another typical case, the dehydrogenated hydrocarbons can be separated from the unconverted dehydrogenatable hydrocarbons by utilizing the inherent capability of the dehydrogenated hydrocarbons to easily enter into several well-known chemical reactions such as alkylation, oligomerization, halogenation, sulfonation, hydration, oxidation, and the like reactions. Irrespective of how the dehydrogenated hydrocarbons are separated from the unreacted hydrocarbons, a stream containing the unreacted dehydrogenatable hydrocarbons will typically be recovered from this hydrocarbon separation step and recycled to the dehydrogenation step. Likewise, the hydrogen phase present in the hydrogen-separating zone will be withdrawn therefrom, a portion of it vented from the system in order to remove the net hydrogen make, and the remaining portion is typically recycled through suitable compressing means to the dehydrogenation step in order to provide diluent hydrogen therefor.

In a preferred embodiment of the present invention wherein long chain normal paraffin hydrocarbons are dehydrogenated to the corresponding normal mono-olefins, a preferred mode of operation of this hydrocarbon recovery step involves an alkylation reaction. In this mode, the hydrocarbon-rich liquid phase withdrawn from the hydrogen-separating zone is combined with a stream containing an alkylatable aromatic and the resulting mixture passed to an alkylation zone containing a suitable highly acid catalyst such as an anhydrous solution of hydrogen fluoride. In the alkylation zone the mono-olefins react with alkylatable aromatic while the unconverted normal paraffins remain substantially unchanged. The effluent stream from the alkylation zone can then be easily separated, typically by means of a suitable fractionation system, to allow recovery of the unreacted normal paraffins. The resulting stream of unconverted normal paraffins is then usually recycled to the dehydrogenation step of the present invention.

The following working examples are introduced to illustrate further the dehydrogenation method and nonacidic multimetallic catalytic composite of the present invention. These examples of specific embodiments of the present invention are intended to be illustrative rather than restrictive.

These examples are all performed in a laboratory scale dehydrogenation plant comprising a reactor, a hydrogen separating zone, heating means, cooling means, pumping means, compressing means, and the like conventional equipment. In this plant, the feed stream containing the dehydrogenatable hydrocarbon is combined with a hydrogen-containing recycle gas stream containing water in an amount corresponding to about 100 wt. ppm. of the hydrocarbon feed and the resultant mixture heated to the desired conversion temperature, which refers herein to the temperature maintained at the inlet to the reactor. The heated mixture is then passed into contact with the instant multimetallic catalyst which is maintained as a fixed bed of catalyst particles in the reactor. The pressures reported herein are recorded at the outlet from the reactor. An effluent stream is withdrawn from the reactor, cooled, and passed into the hydrogen-separating zone wherein a hydrogen-containing gas phase separates from a hydrocarbon-rich liquid phase containing dehydrogenated hydrocarbons, unconverted dehydrogenatable hydrocarbons, and a minor amount of side products of the dehydrogenation reaction. A portion of the hydrogen-containing gas phase is recovered as excess recycle gas with the remaining portion being continuously recycled, after water addition as needed, through suitable compressing means to the heating zone as described above. The hydrocarbon-rich liquid phase from the separating zone is withdrawn therefrom and subjected to analysis to determine conversion and selectivity for the desired dehydrogenated hydrocarbon as will be indicated in the Examples. Conversion numbers of the dehydrogenatable hydrocarbon reported herein are all calculated on the basis of disappearance of the dehydrogenatable hydrocarbon and are expressed in mole percent. Similarly, selectivity numbers are reported on the basis of moles of desired hydrocarbon produced per 100 moles of dehydrogenatable hydrocarbon converted.

All of the catalysts utilized in these examples are prepared according to the following preferred method with suitable modification in stoichiometry to achieve the compositions reported in each example. First, an alumina carrier material comprising 1/16 inch spheres having an apparent bulk density of about 0.3 g/cc is prepared by: forming an alumina hydroxyl chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel, aging, and washing the resulting particles with an ammoniacal solution and finally drying, calcining, and steaming the aged and washed particles to form spherical particles of gamma-alumina containing substantially less than 0.1 wt. % combined chloride. Additional details as to this method of preparing this alumina carrier material are given in the teachings of U.S. Pat. No. 2,620,314.

The resulting gamma-alumina particles are then contacted in a first impregnation step at suitable impregnation conditions with a first aqueous impregnation solution containing chloroplatinic acid, cadmium nitrate and nitric acid in amounts sufficient to yield a final multimetallic catalytic composite containing a uniform dispersion of the hereinafter specified amounts of platinum and cadmium. The nitric acid is utilized in an amount of about 5 wt. % of the alumina particles. In order to ensure a uniform dispersion of the metallic components in the carrier material, the impregnation solution is maintained in contact with the carrier material particles for about ½ hour at a temperature of about 70° F. with constant agitation. The impregnated spheres are then dried at a temperature of about 225° F. for about an hour and thereafter calcined or oxidized in an air atmosphere containing about 5 to 25 vol. % $H_2O$ at a temperature of about 500° F. to about 1000° F. (preferably about 800° to 950° F.) for about 2 to 10 hours effective to convert all of the metallic components to the corresponding oxide forms. In general, it is a good practice to thereafter treat the resulting oxidized particles with an air stream containing about 10 to about 30% steam at a temperature of about 800° F. to about 1000° F. for an additional period of about 1 to about 5 hours in order to reduce any residual combined chloride contained in the catalyst to a value of less than 0.5 wt. % and preferably less than 0.2 wt. %.

The cobalt component is thereafter added to this oxidized and steam-stripped catalyst in a second impregnation step. In the cases shown in the examples where the catalyst utilized contains an alkali or alkaline earth component, this component is also added to the oxidized and steam-treated multimetallic catalyst in this second impregnation step. This second impregnation step involves contacting the oxidized and steamed multimetallic catalyst with an aqueous acidic solution of a suitable soluble and decomposable salt of cobalt and of the alkali or alkaline earth component (when it is to be added) under conditions selected to result in a uniform dispersion of these components in the carrier material. For the catalysts utilized in the present examples, the salts are cobalt nitrate or acetate and either lithium nitrate or potassium nitrate. The amounts of the salts of cobalt and of the alkali metal utilized are chosen to result in a final catalyst containing the required amount of cobalt and having the desired nonacidic characteristics. The resulting cobalt and alkali or alkaline earth-impregnated particles are then preferably dried and oxidized in an air atmosphere in much the same manner as is described above following the first impregnation step. In some cases, it is possible to combine both of these impregnation steps into a single step, thereby significantly reducing the time and complexity of the catalyst manufacturing procedure.

The resulting oxidized catalyst is thereafter subjected to a drying step which involves contacting the oxidized particles with a dry air stream at a temperature of about 930° F., a GHSV of 300 $hr.^{-1}$ for a period of about 10 hours. The dried catalyst is then purged with a dry nitrogen stream and thereafter selectively reduced by contacting with a dry hydrogen stream at conditions including a temperature of about 870° F., atmospheric pressure and a gas hourly space velocity of about 500 $hr.^{-1}$, for a period of about 1 to 10 hours effective to at least reduce substantially all of the platinum group component to the corresponding elemental metal, while maintaining the alkali or alkaline earth and cadmium components in a positive oxidation state.

EXAMPLE I

The reactor is loaded with 100 cc of a catalyst containing, on an elemental basis, 0.3 wt. % platinum, 1.0 wt. % cobalt and 0.15 wt. % cadmium and less than 0.15 wt. % chloride. This corresponds to an atomic ratio of cadmium to platinum of 0.87:1 and of cobalt to platinum of 11:1. The feed stream utilized is commercial grade isobutane containing 99.7 wt. % isobutane and 0.3 wt. % normal butane. The feed stream is contacted with the catalyst at a temperature of 1020° F., a pressure of 10 psig., a liquid hourly space velocity of 4.0 hr.$^{-1}$, and a recycle gas to hydrocarbon mole ratio of 3:1. The dehydrogenation plant is lined-out at these conditions and a 20 hour test period commenced. The hydrocarbon product stream from the plant is continuously analyzed by GLC (gas liquid chromatography) and a high conversion of isobutane is observed with a high selectivity for isobutylene.

EXAMPLE II

The catalyst contains, on an elemental basis, 0.375 wt. % platinum, 0.5 wt. % cobalt, 0.1 wt. % cadmium, 0.6 wt. % lithium, and 0.15 wt. % combined chloride. These amounts correspond to the following atomic ratios: (1) Cd/Pt of 0.46:1, (2) Co/Pt of 4.4:1, and (3) Li/Pt of 45:1. The feed stream is commercial grade normal dodecane. The dehydrogenation reactor is operated at a temperature of 850° F., a pressure of 10 psig., a liquid hourly space velocity of 32 hr.$^{-1}$, and a recycle gas to hydrocarbon mole ratio of 5:1. After a line-out period, a 20 hour test period is performed during which the average conversion of the normal dodecane is maintained at a high level with a selectivity for normal dodecene of about 90%.

EXAMPLE III

The catalyst is the same as utilized in Example II. The feed stream is normal tetradecane. The conditions utilized are a temperature of 830° F., a pressure of 20 psig., a liquid hourly space velocity of 32 hr.$^{-1}$, and a recycle gas to hydrocarbon mole ratio of 4:1. After a line-out period, a 20 hour test shows an average conversion of about 12%, and a selectivity for normal tetradecene of about 90%.

EXAMPLE IV

The catalyst contains, on an elemental basis, 0.3 wt. % platinum, 1.0 wt. % cobalt, 0.15 wt. % cadmium, and 0.6 wt. % lithium, with combined chloride being less than 0.2 wt. %. The pertinent atomic ratios are: (1) Cd/Pt of 0.87:1, (2) Co/Pt of 11:1, and (3) Li/Pt of 56:1. The feed stream is substantially pure cyclohexane. The conditions utilized are a temperature of 900° F., a pressure of 100 psig., a liquid hourly space velocity of 3.0 hr.$^{-1}$, and a recycle gas to hydrocarbon mole ratio of 4:1. After a line-out period, a 20 hour test is performed with almost quantitative conversion of cyclohexane to benzene and hydrogen.

EXAMPLE V

The catalyst contains, on an elemental basis, 0.2 wt. % platinum, 0.5 wt. % cobalt, 0.2 wt. % cadmium, 1.5 wt. % potassium, and less than 0.2 wt. % combined chloride. The governing atomic ratios are: (1) Cd/Pt of 1.74:1, (2) Co/Pt of 8.3:1 and (3) K/Pt of 37:1. The feed stream is commercial grade ethylbenzene. The conditions utilized are a pressure of 15 psig., a liquid hourly space velocity of 32 hr.$^{-1}$, a temperature of 1010° F., and a recycle gas to hydrocarbon mole ratio of 3:1. During a 20 hour test period, 85% or more of equilibrium conversion of the ethylbenzene is observed. The selectivity for stryrene is about 90%.

It is intended to cover by the following claims, all changes and modifications of the above disclosure of the present invention which would be self-evident to a man of ordinary skill in the catalyst-formulation art or in the hydrocarbon dehydrogenation art.

I claim as my invention:

1. A method for dehydrogenating a dehydrogenatable hydrocarbon comprising contacting the hydrocarbon, at hydrocarbon dehydrogenation conditions, with a nonacidic catalytic composite consisting essentially of a porous carrier material containing, on an elemental basis, about 0.01 to about 2 wt. % platinum group metal, about 0.05 to about 5 wt. % cobalt, about 0.1 to about 5 wt. % alkali metal or alkaline earth metal and about 0.01 to about 5 wt. % cadmium; wherein the platinum group, catalytically available cobalt, cadmium, and alkali or alkaline earth components are uniformly dispersed throughout the porous carrier material; wherein substantially all of the platinum group component is present in the elemental metallic state; wherein substantially all of the cadmium and alkali or alkaline earth components are present in an oxidation state above that of the corresponding elemental metal; and wherein substantially all of the catalytically available cobalt component is present in the elemental metallic state or in a state which is reducible to the elemental metallic state under the hydrocarbon dehydrogentaion conditions or in a mixture of these states.

2. A method as defined in claim 1 wherein the dehydrogenatable hydrocarbon is admixed with hydrogen when it contacts the nonacidic catalytic composite.

3. A method as defined in claim 1 wherein the platinum group component is platinum.

4. A method as defined in claim 1 wherein the platinum group component is iridium.

5. A method as defined in claim 1 wherein the platinum group component is rhodium.

6. A method as defined in claim 1 wherein the platinum group component is palladium.

7. A method as defined in claim 1 wherein the catalytic composite is in a sulfur-free state.

8. A method as defined in claim 1 wherein the porous carrier material is a refractory inorganic oxide.

9. A method as defined in claim 8 wherein the refractory inorganic oxide is alumina.

10. A method as defined in claim 1 wherein the alkali or alkaline earth component is lithium oxide.

11. A method as defined in claim 1 wherein the alkali or alkaline earth component is lithium oxide.

12. A method as defined in claim 1 wherein the composite contains, on an elemental basis, about 0.05 to about 1 wt. % platinum group metal, about 0.1 to about 2.5 wt. % cobalt, about 0.05 to about 1 wt. % cadmium and about 0.25 to about 3.5 wt. % alkali metal or alkaline earth metal.

13. A method as defined in claim 1 wherein the metals contents thereof is adjusted so that the atomic ratio of cadmium to platinum group metal is about 0.1:1 to about 5:1, the atomic ratio of alkali metal or alkaline earth metal to platinum group metal is about 5:1 to about 100:1 and the atomic ratio of cobalt to platinum group metal is about 0.1:1 to 66:1.

14. A method as defined in claim 1 wherein substantially all of the cadmium component is present in the catalytic composite in the form of cadmium oxide or cadmium aluminate or mixtures thereof.

15. A method as defined in claim 2 wherein substantially all of the catalytically available cobalt component contained in the composite is present in the elemental metallic state after the method is started-up and lined-out at the hydrocarbon dehydrogenation conditions.

16. A method as defined in claim 1 wherein the dehydrogenatable hydrocarbon is an aliphatic hydrocarbon containing 2 to 30 carbon atoms per molecule.

17. A method as defined in claim 1 wherein the dehydrogenatable hydrocarbon is a normal paraffin hydrocarbon containing 4 to 30 carbon atoms per molecule.

18. A method as defined in claim 1 wherein the dehydrogenatable hydrocarbon is naphthene.

19. A method as defined in claim 1 wherein the dehydrogenatable hydrocarbon is an alkylaromatic, the alkyl group of which contains about 2 to 6 carbon atoms.

20. A method as defined in claim 2 wherein the dehydrogenation conditions include a temperature of 700° to about 1200° F., a pressure of 0.1 to 10 atmospheres, an LHSV of 1 to 40 hr.$^{-1}$, and a hydrogen to hydrocarbon mole ratio of about 1:1 to about 20:1.

21. A method as defined in claim 1 wherein the contacting is performed in the presence of water or a water-producing substance in an amount corresponding to about 1 to about 1000 wt. ppm. based on hydrocarbon charged.

* * * * *